US008906042B2

(12) United States Patent
Hodgkinson et al.

(10) Patent No.: US 8,906,042 B2
(45) Date of Patent: Dec. 9, 2014

(54) WOUND CLOSURE DEVICE INCLUDING MESH BARRIER

(75) Inventors: Gerald Hodgkinson, Guilford, CT (US); Timothy D. Ebner, North Haven, CT (US)

(73) Assignee: Covidien LP, Mansfield, MA (US)

( * ) Notice: Subject to any disclaimer, the term of this patent is extended or adjusted under 35 U.S.C. 154(b) by 666 days.

(21) Appl. No.: 13/117,317

(22) Filed: May 27, 2011

(65) Prior Publication Data

US 2012/0029532 A1 Feb. 2, 2012

Related U.S. Application Data

(60) Provisional application No. 61/368,815, filed on Jul. 29, 2010.

(51) Int. Cl.
*A61B 17/04* (2006.01)
*A61B 17/08* (2006.01)
*A61B 17/00* (2006.01)

(52) U.S. Cl.
CPC ... *A61B 17/0057* (2013.01); *A61B 2017/00597* (2013.01); *A61B 2017/00623* (2013.01); *A61B 2017/00637* (2013.01); *A61B 17/0482* (2013.01); *A61B 2017/0061* (2013.01); *A61B 2017/00663* (2013.01); *A61B 17/0469* (2013.01)
USPC .......................................... 606/144; 606/151

(58) Field of Classification Search
CPC .......... A61B 17/0057; A61B 17/0482; A61B 17/0469; A61B 2017/00597; A61B 2017/0061; A61B 2017/00623; A61B 2017/00637; A61B 2017/00663
USPC ............ 606/139, 144, 145, 148, 151; 600/29, 600/30, 37
See application file for complete search history.

(56) References Cited

U.S. PATENT DOCUMENTS

| | | | |
|---|---|---|---|
| 4,007,743 A | 2/1977 | Blake | |
| 4,733,664 A | 3/1988 | Kirsch et al. | |
| 5,397,332 A * | 3/1995 | Kammerer et al. | 606/151 |
| 5,470,338 A | 11/1995 | Whitfield et al. | |
| 5,507,755 A * | 4/1996 | Gresl et al. | 606/139 |

(Continued)

FOREIGN PATENT DOCUMENTS

| | | | |
|---|---|---|---|
| EP | 1354558 A2 | 10/2003 | |
| EP | 1629780 A1 | 3/2006 | |

(Continued)

OTHER PUBLICATIONS

European Search Report for EP 11250682.9-1269 date of completion is Oct. 17, 2011 (3 pages).

*Primary Examiner* — Julian W Woo

(57) ABSTRACT

A suturing device includes an elongate shaft defining a longitudinal axis, a trajectory guide translatably mounted on the elongate shaft and an introducer guard member operatively coupled to a distal portion of the elongate shaft. The introducer guard member includes at least one arm member which is movable between a first position in which the arm member is retracted, substantially in alignment with the longitudinal axis and a second position in which the at least one arm member is deployed. The introducer guard member includes an attaching member for releasably retaining a suture. The trajectory guide defines at least one bore therethrough. The bore obliquely extends through the trajectory guide and defines an angle with respect to the longitudinal axis. The bore aligns with the attaching member when the introducer guard member is in the second position.

22 Claims, 11 Drawing Sheets

(56) References Cited

U.S. PATENT DOCUMENTS

| | | | |
|---|---|---|---|
| 6,024,748 | A | 2/2000 | Manzo et al. |
| 6,036,699 | A * | 3/2000 | Andreas et al. ............... 606/139 |
| 6,117,144 | A | 9/2000 | Nobles et al. |
| 6,296,648 | B1 | 10/2001 | Boche et al. |
| 6,743,241 | B2 | 6/2004 | Kerr |
| 6,911,034 | B2 | 6/2005 | Nobles et al. |
| 7,160,309 | B2 | 1/2007 | Voss |
| 7,211,093 | B2 | 5/2007 | Sauer et a |
| 7,235,087 | B2 | 6/2007 | Modesitt et al. |
| 7,449,024 | B2 | 11/2008 | Stafford |
| 7,736,388 | B2 | 6/2010 | Goldfarb et al. |
| 7,740,640 | B2 | 6/2010 | Ginn |
| 7,951,158 | B2 * | 5/2011 | Catanese et al. ............... 606/151 |
| 2001/0031973 | A1 | 10/2001 | Nobles et al. |
| 2004/0044365 | A1 | 3/2004 | Bachman |
| 2004/0097982 | A1 | 5/2004 | Jugenheimer et al. |
| 2005/0154402 | A1 | 7/2005 | Sauer et al. |
| 2005/0251175 | A1 | 11/2005 | Weisenburgh, II et al. |
| 2005/0288707 | A1 | 12/2005 | De Canniere et al. |
| 2006/0030868 | A1 | 2/2006 | Bennett, III |
| 2006/0069397 | A1 | 3/2006 | Nobles et al. |
| 2006/0224168 | A1 | 10/2006 | Weisenburgh, II et al. |
| 2008/0033459 | A1 | 2/2008 | Shafi et al. |
| 2008/0045979 | A1 | 2/2008 | Ma |
| 2009/0105729 | A1 | 4/2009 | Zentgraf |
| 2009/0143808 | A1 | 6/2009 | Houser |
| 2009/0157105 | A1 | 6/2009 | Zung et al. |
| 2011/0082475 | A1 | 4/2011 | Smith |
| 2011/0082477 | A1 | 4/2011 | Smith |
| 2011/0082480 | A1 | 4/2011 | Viola |
| 2011/0112553 | A1 | 5/2011 | Smith |
| 2012/0035623 | A1 * | 2/2012 | Bagaoisan et al. ............ 606/144 |

FOREIGN PATENT DOCUMENTS

| | | |
|---|---|---|
| WO | WO 02/24078 A1 | 3/2002 |
| WO | WO 2010/081096 A2 | 7/2010 |
| WO | WO 2010/085793 A2 | 7/2010 |
| WO | WO 2010/105046 A1 | 9/2010 |

* cited by examiner

WOUND CLOSURE DEVICE INCLUDING MESH BARRIER

CROSS-REFERENCE TO RELATED APPLICATIONS

This application claims priority to, and the benefit of, U.S. Provisional Patent Application No. 61/368,815, filed Jul. 29, 2010, the entire contents of which are hereby incorporated by reference.

BACKGROUND

1. Technical Field

The present disclosure relates to a wound closure device and, more particularly, to a wound closure device for suturing an opening in tissue.

2. Background of Related Art

During endoscopic surgical procedures, for example, a trocar device is utilized to puncture the peritoneum to provide an access port by way of a cannula through the abdominal wall. Generally, a trocar and/or cannula is placed through the abdominal wall for introduction of surgical instrumentation which is necessary to carry out the surgical procedure. In this manner, the surgeon may introduce a surgical instrument such as a grasper, scissor, clip applier, stapler or any other surgical instrument which may be necessary during the particular surgical procedure. Once the procedure is complete, it is necessary to close the wound.

Conventional instruments for closing puncture wounds generally include a shaft that can be extended into the body through either the puncture wound itself (in the case of a puncture caused by trauma) or through a cannula (in the case of a puncture created to access a surgical site). Suture retaining needles are then deployed from the shaft into tissue. Unfortunately, the mechanisms used for deploying the needles are often cumbersome and may make the extension and/or retraction of the suturing device difficult.

SUMMARY

In accordance with the present disclosure, a suturing device is provided. The suturing device includes an elongate shaft defining a longitudinal axis, a trajectory guide mounted on the elongate shaft and an introducer guard member operatively coupled to the elongate shaft. The trajectory guide defines at least one bore therethrough. The introducer guard member includes at least one arm member that is movable between a first position in which the arm member is retracted, substantially in alignment with the longitudinal axis and a second position in which the at least one arm member is deployed, defining an angle with respect to the longitudinal axis.

In an embodiment, the arm member is hingedly connected to the elongate shaft. In particular, the arm member may be hingedly connected to a distal portion of the elongate shaft.

In another embodiment, the trajectory guide is translatable along the elongate shaft. The trajectory guide may include a locking mechanism for securely anchoring the trajectory guide to a position along the elongate shaft. The bore defined in the trajectory guide obliquely extends therein with respect to the longitudinal axis.

In yet another embodiment, the arm member includes an attaching member configured for releasably retaining a suture. The attaching member is on a first surface of the arm member. The bore is aligned with the attaching member when the arm member is in the second position.

In still another embodiment, the arm member includes an attaching member configured for releasably retaining a suture. The attaching member is disposed adjacent a distal end of the arm member. The bore is aligned with the attaching member when the arm member is in the second position.

In still another embodiment, the suturing device further includes a mesh disposed on a second surface of the arm member when the arm member is in the second position. The suture attaches the mesh against the second surface of the arm member when the arm member is in the second position.

In still another embodiment, the suturing device further includes a cannulated needle defining a lumen therethrough. The bore of the trajectory guide is dimensioned for receiving the cannulated needle therethrough. The suturing device may further include a rod. The lumen of the cannulated needle is configured for receiving the rod therethrough. The rod may include catching structure for capturing the suture releasably retained by the attaching member. The catching structure is disposed at a distal portion of the rod. The catching structure may be a hook.

In still another embodiment, the introducer guard member in the second position is substantially orthogonal with respect to the longitudinal axis.

In still another embodiment, the trajectory guide is longitudinally tapered with respect to a width thereof.

In an alternative embodiment, the introducer guard member is longitudinally tapered with respect to a width thereof. Moreover, the arm member may be longitudinally tapered with respect to a width thereof.

BRIEF DESCRIPTION OF THE DRAWINGS

Various embodiments of the presently disclosed suturing instrument are described herein with references to the accompanying drawings, wherein.

DETAILED DESCRIPTION OF THE EMBODIMENTS

Figure 1:
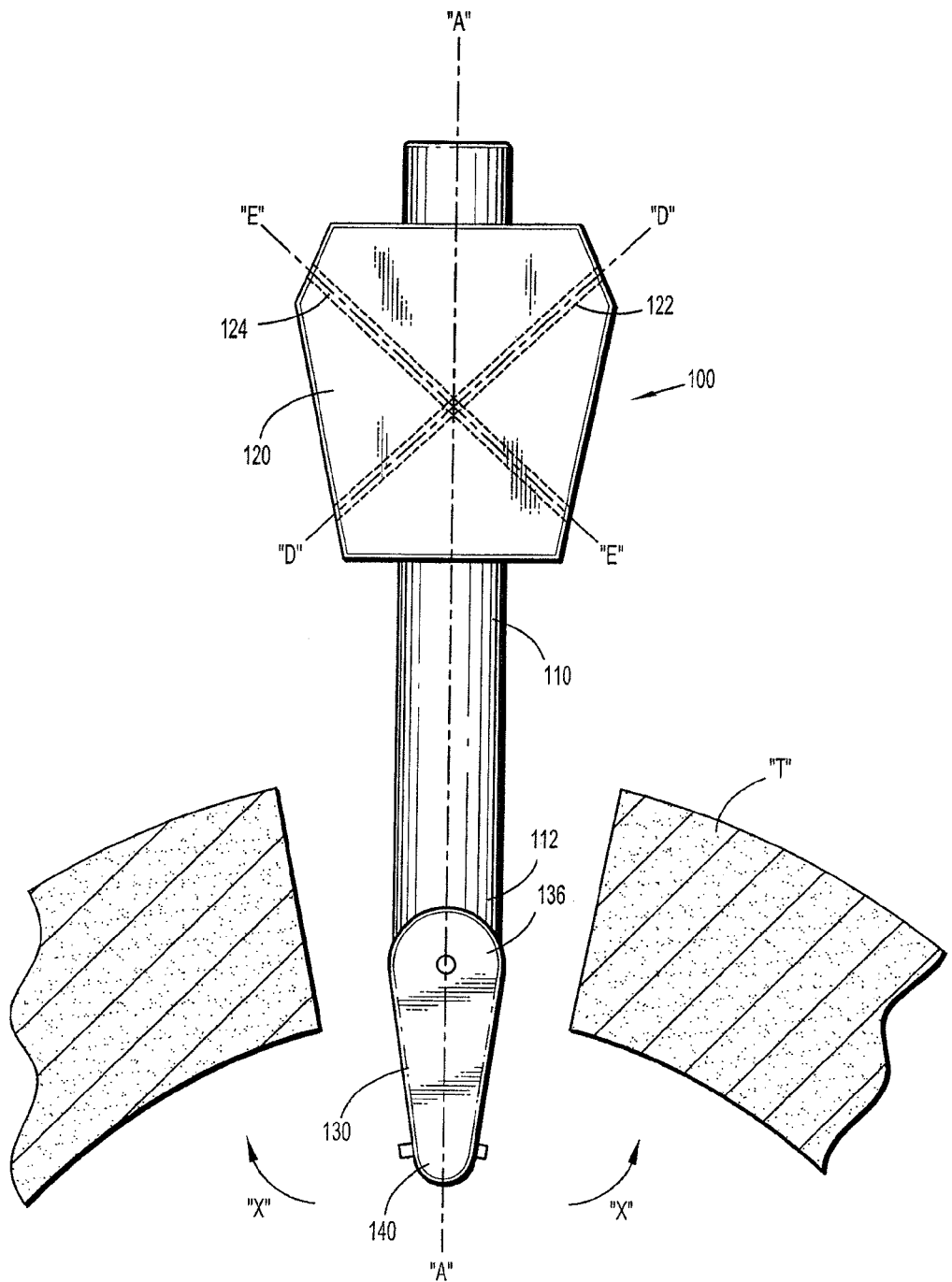
FIG. 1 is a side view of a suturing device in accordance with the present disclosure disposed in an opening in tissue.

Various exemplary embodiments of the presently disclosed surgical device will now be described in detail with reference to the drawings wherein like reference numerals identify similar or identical elements. In the drawings and in the description which follows, the term "proximal" will refer to the end of the component that is closer to the operator during use, while the term "distal" will refer to the end of the component that is farther from the operator, as is traditional and conventional in the art.

Figure 2:
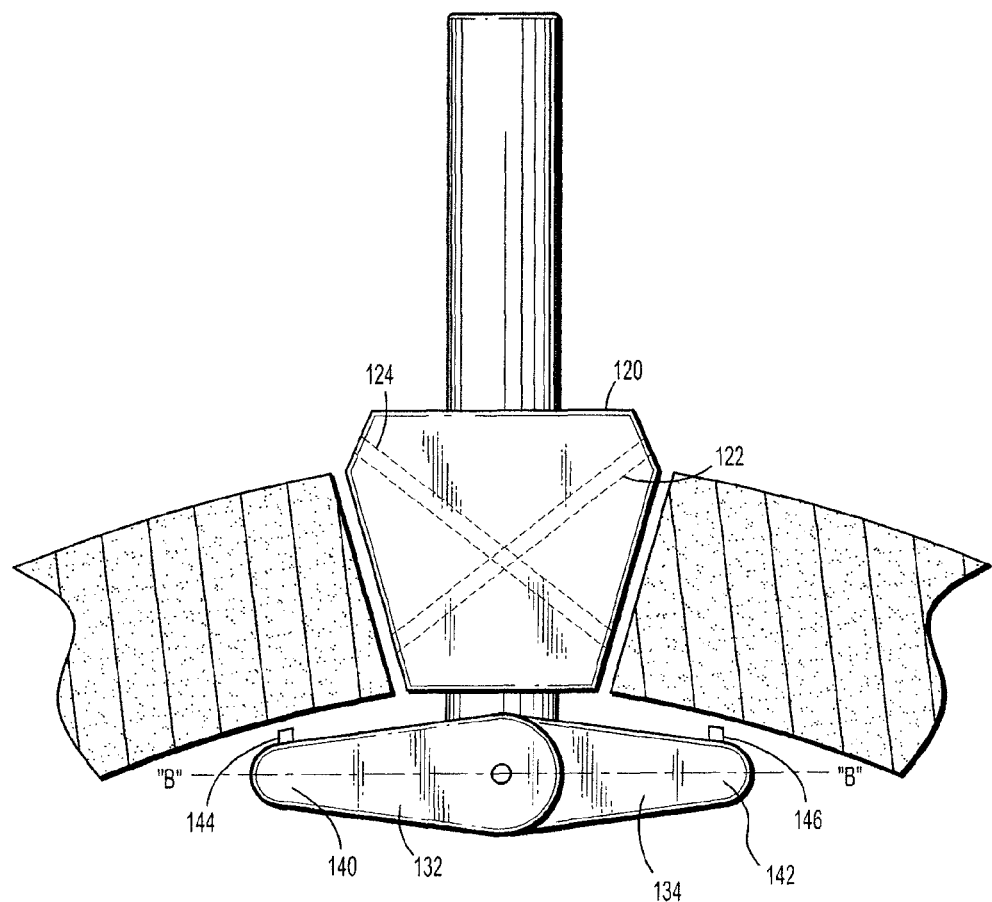
FIG. 2 is a side view of the suturing device of FIG. 1 illustrating an introducer guard member thereof in a deployed state.

With reference to FIGS. 1 and 2, a suturing instrument 100 generally includes an elongate shaft 110 defining a longitudinal axis "A-A," a trajectory guide 120 translatably mounted on elongate shaft 110, and an introducer guard member 130 operatively coupled to a distal end portion 112 of elongate shaft 110. Trajectory guide 120 is translatably mounted on elongate shaft 110 and includes a locking mechanism (not shown) that securely anchors trajectory guide 120 to a desired position along elongate shaft 110. Thus, the distance between trajectory guide 120 and introducer guard member 130 may be adjusted based on the anatomy of the patient. Introducer guard member 130 includes a pair of arm members 132, 134. As will be discussed in greater detail below, arm members 132, 134 are movable from a first position in which arm member 132, 134 are retracted, substantially in alignment with longitudinal axis "A-A" as shown in FIG. 1 to a second position in which arm members 132, 134 are deployed, defining a transverse axis "B-B" as shown in FIG. 2 or an acute angle with respect to the longitudinal axis "A-A," for example.

Figure 4:
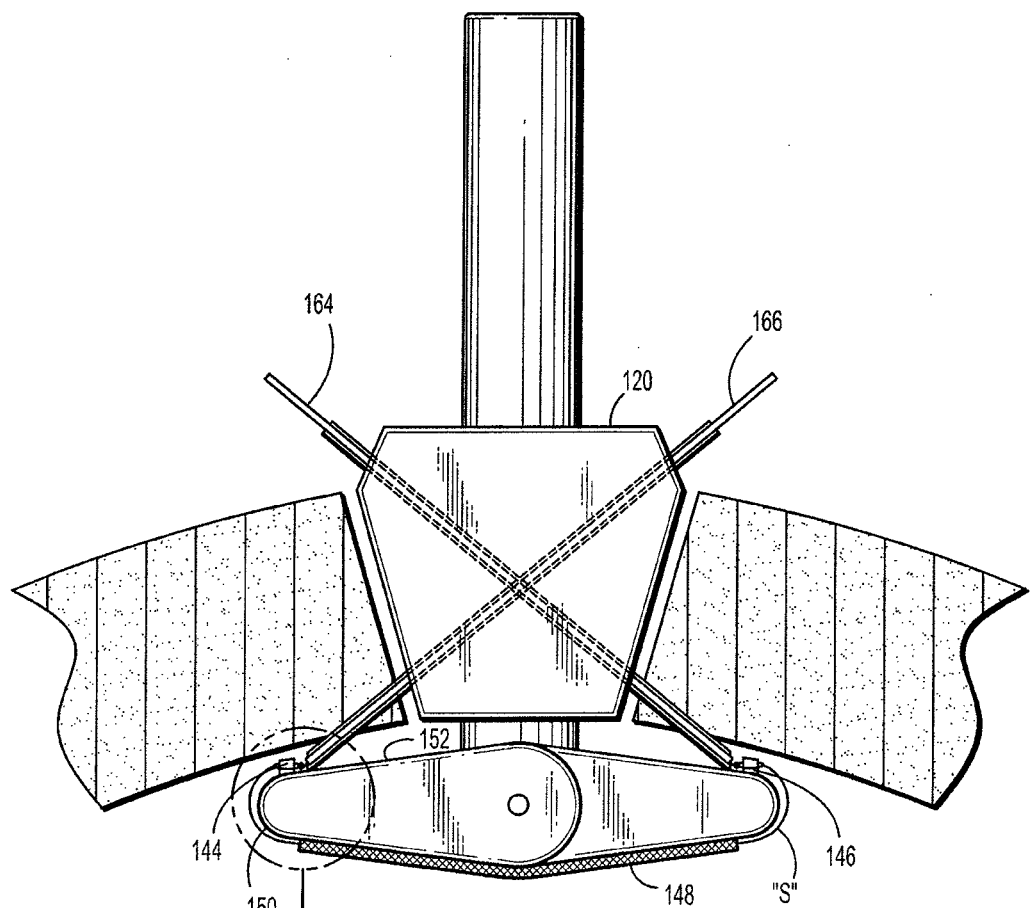
FIG. 4 is a side view of the suturing device of FIG. 3 having a pair of rods inserted through the pair of cannulated needles.

With continued reference to FIGS. 1 and 2, trajectory guide 120 includes a generally tapered configuration to facilitate insertion/removal thereof into an opening in tissue "T." Trajectory guide 120 defines bores 122, 124 (shown in phantom for illustrative purposes) that extend obliquely from a proximal end portion thereof to a distal end portion thereof, thereby forming an angle with respect to longitudinal axis "A-A." Bores 122, 124 define longitudinal axes "D-D," "E-E," respectively. Bores 122, 124 may be dimensioned to receive one or more types of surgical instruments, e.g., surgical instruments configured to manipulate a suture. The angle defined by each bore 122, 124 with respect to longitudinal axis "A-A" may be tailored to meet the needs of a particular procedure such that bores 122, 124 in conjunction with introducer guard member 130 provide proper configuration for suture "S" to pierce through tissue "T," as shown in FIG. 4. For example, a greater degree of angle needs to be selected if a wider mesh 148 is to be chosen, in order to ensure that mesh 148 tightly covers against the posterior side of the opening of tissue "T." Moreover, by choosing a greater degree of angle, suture "S" enters the posterior side of tissue "T" away from the opening in tissue "T" which may inhibit tearing of sutured tissue "T." It is also envisioned that additional bores may be defined in trajectory guide 120 to further accommodate other surgical instruments through trajectory guide 120.

With continued reference to FIGS. 1 and 2, introducer guard member 130 is operatively connected to distal end portion 112 of elongate shaft 110. In the illustrated embodiment, proximal end 136 of arm member 132 is hingedly coupled to distal end portion 112 of elongate shaft 110 such that arm member 132 can be hingedly retracted, substantially in alignment with longitudinal axis "A-A" in order to facilitate insertion/removal of introducer guard member 130 through the opening of tissue "T." A proximal end of arm member 134 is substantially similar and is not shown. Hingedly coupled arm members 132, 134 can also be deployed in the direction of arrows "X" shown in FIG. 1, such that deployed arm members 132, 134 define a transverse axis "B-B." As shown in FIG. 2, deployed arm members 132, 134 are substantially orthogonal to longitudinal axis "A-A."

Figure 3:
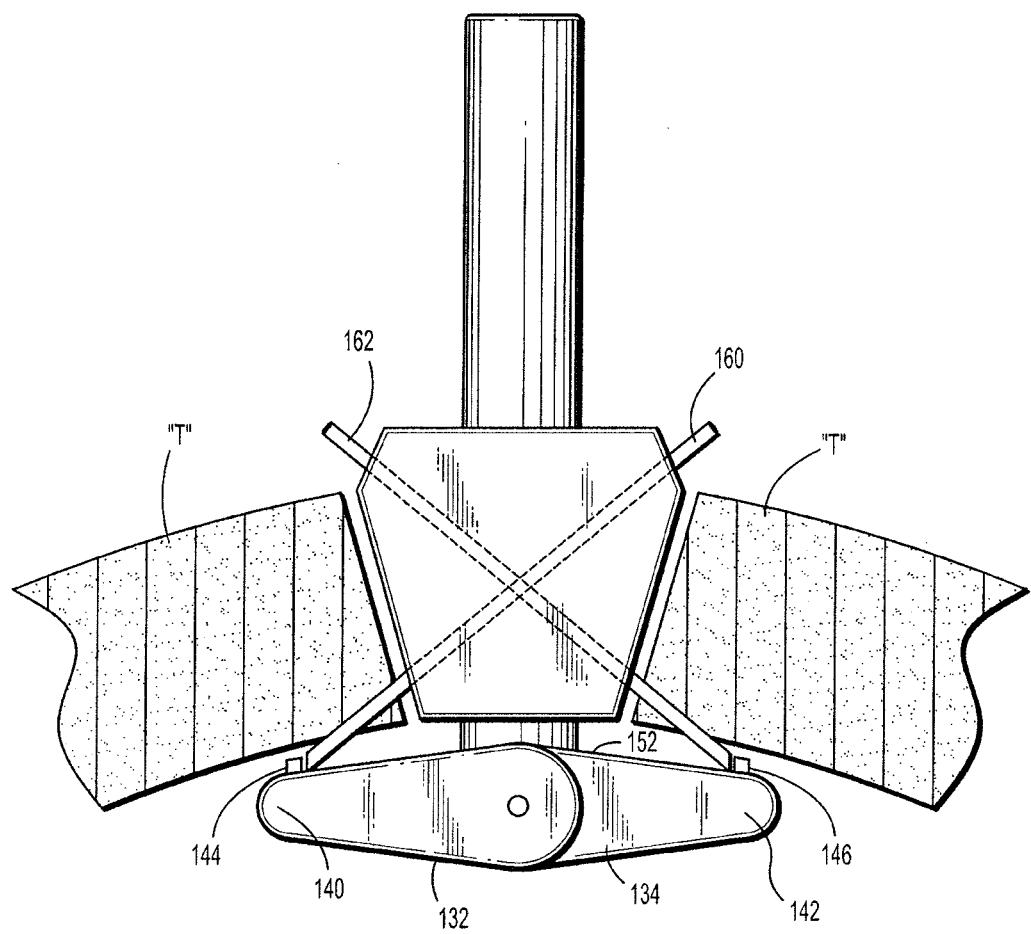
FIG. 3 is a side view of the suturing device of FIG. 2 having a pair of cannulated needles inserted through a trajectory guide of the suturing device.
Figure 4A:
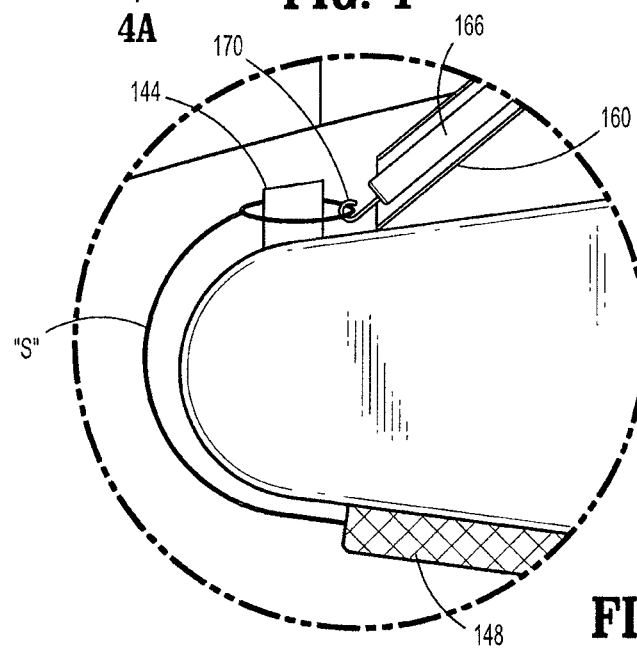
FIG. 4A is an enlarged view of the indicated area of detail of FIG. 4.
Figure 4B:
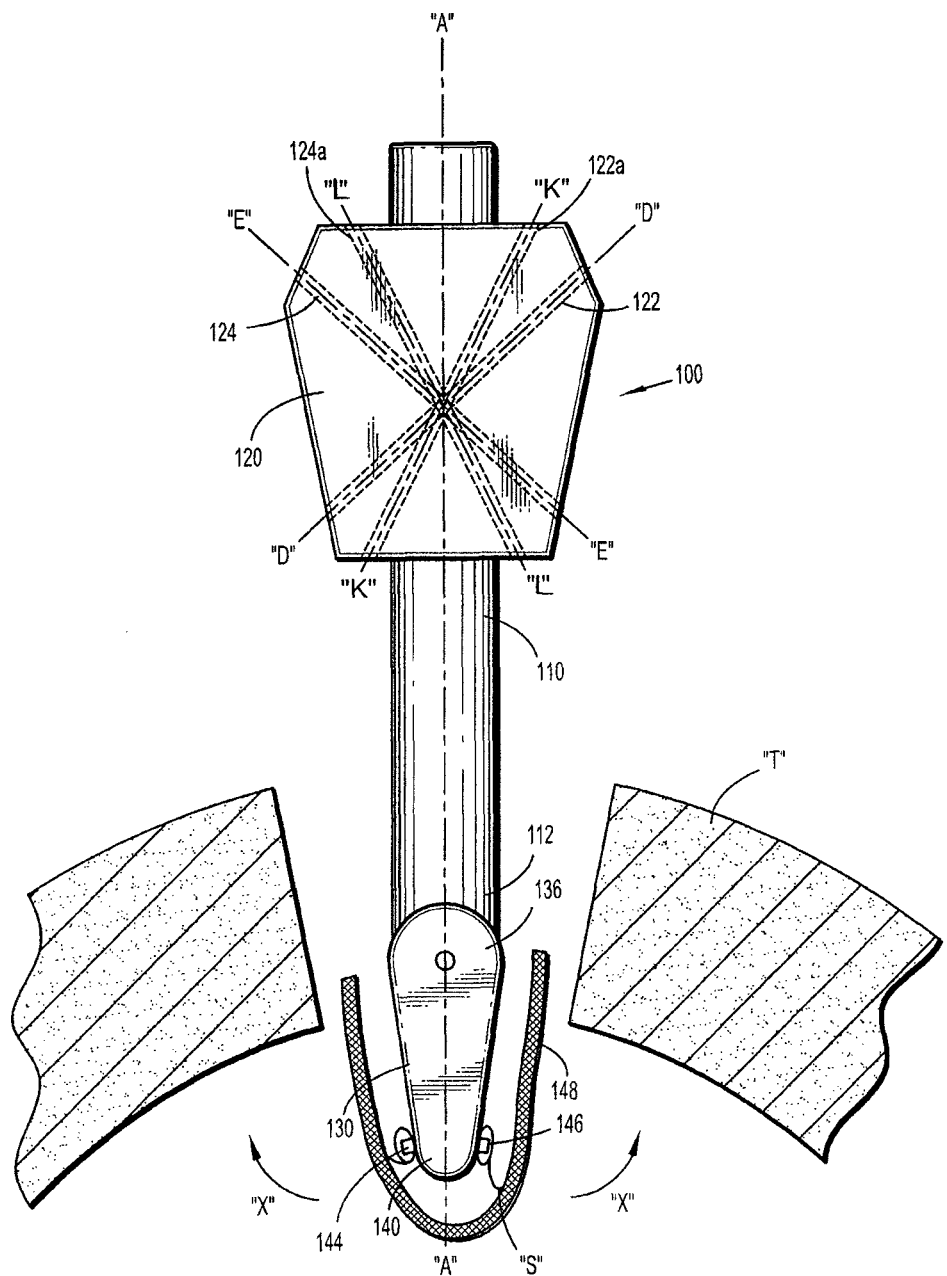
FIG. 4B is a side view of the suturing device of FIG. 1 illustrating a mesh attached to the introducer guard member in a retracted state.
Figure 4C:
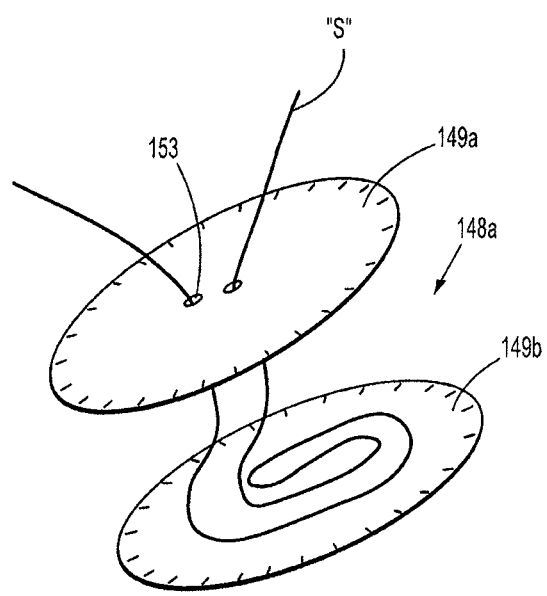
FIG. 4C is a perspective view of a two-piece mesh with parts separated.
Figure 5:
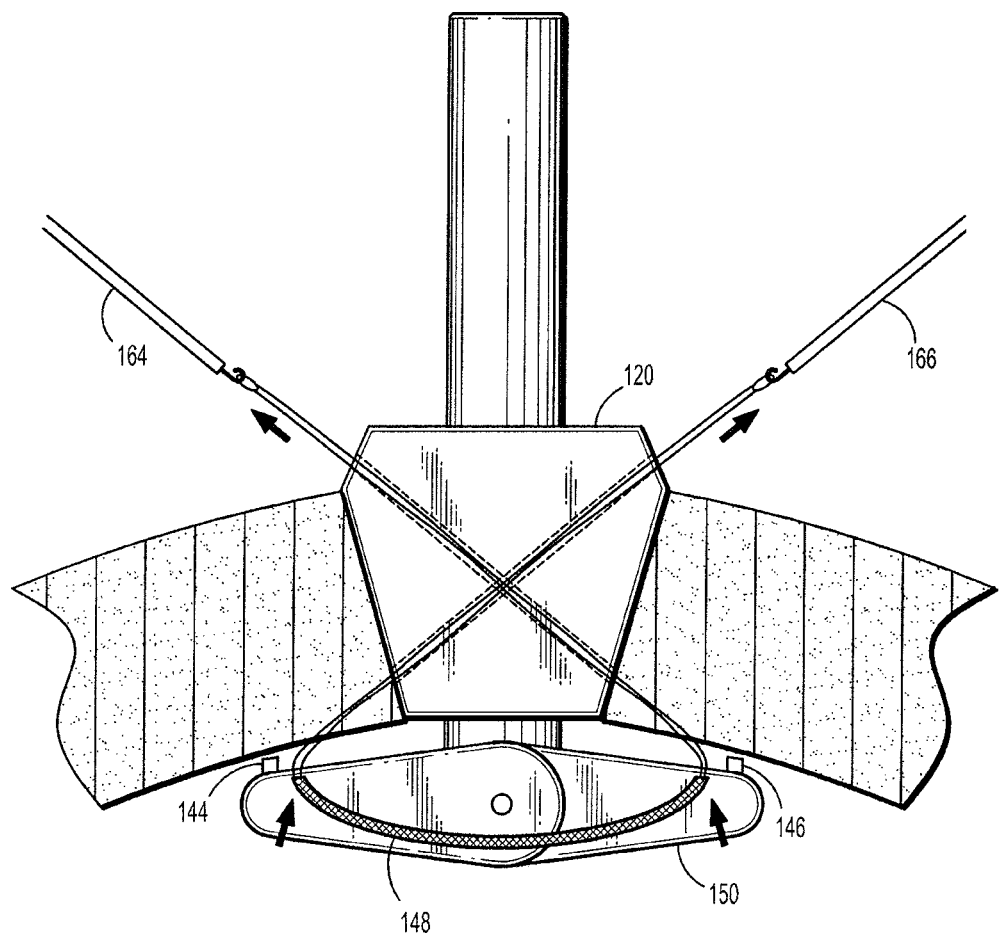
FIG. 5 is a side view of the suturing device of FIG. 4 illustrating extraction of looped ends of a suture.

With reference now to FIGS. 3-5, there is illustrated introducer guard member 130 including a pair of attaching members 144, 146 on a first surface 152 of arm members 132, 134, and more particularly, disposed adjacent free ends 140, 142 of arm members 132, 134, respectively. Attaching members 144, 146 may be in a form of prongs or pins configured to releasably retain the ends of suture "S," as shown in FIGS. 4 and 4A. Each end of suture "S" may, for example, form a loop so that suture "S" can be releasably anchored to each of attaching members 144, 146 as shown in FIGS. 4 and 4A. In the alternative, a slit dimensioned to secure or wedge a portion of suture "S" to free ends 140, 142 of arm members 132, 134 may be utilized such that when arm members 132, 134 are deployed from the first position to the second position, suture "S" is not dislodged or released from the slit. Additionally, introducer guard member 130 includes a mesh 148 at least partially enclosing introducer guard member 130 when introduced into the opening in tissue "T," as shown in FIG. 4B. Mesh 148 is connected to suture "S" which secures mesh 148 to introducer guard member 130 by having each end of suture "S" anchored to each of attaching members 144, 146. Low tack adhesive may be used on mesh 148 to releasably hold surplus suture "S" on mesh 148 such that surplus suture "S" does not interfere with the procedure being performed. Alternatively, surplus suture "S" may be housed in a pocket defined by a two-piece mesh 148a welded on the edges, as shown in FIG. 4C. Two-piece mesh 148a includes an upper mesh portion 149a and a lower mesh portion 149b. Upper mesh portion 149a defines holes 153 through which ends of suture "S" pass. Surplus suture "S" allows arm members 132, 34 to move from the first position to the second position without tearing suture "S" or mesh 148a. As such, surplus suture "S" housed in the pocket does not interfere with the procedure being performed when arm members 132, 134 are in the first position.

As arm members 132, 134 are deployed in the opening in tissue "T," surplus suture "S" is released from mesh 148 and mesh 148 becomes disposed on a second surface 150 of introducer guard member 130 as shown in FIG. 4. Mesh 148 may be made of absorbable material and/or any suitable biocompatible material. Mesh 148 provides prophylaxis against incisional hernia.

In the embodiment illustrated in FIGS. 3-5, a pair of cannulated needles 160, 162 each defining a lumen therethrough are provided in bores 122, 124 of trajectory guide 120. Cannulated needles 160, 162 are dimensioned to slidably extend through bores 122, 124 of trajectory guide 120, respectively. When introducer guard member 130 is in the second position, i.e., arm members 132, 134 are deployed, longitudinal axis "D-D," "E-E" are in alignment with attaching members 144, 146, respectively. Cannulated needles 160, 162 are provided to extend through bores 122, 124 and pierce through tissue "T" (e.g., a fascia of an abdominal cavity). Cannulated needles 160, 162 move through tissue "T" and further extend distally until reaching first surface 152 of introducer guard member 130. Attaching members 144, 146 that serve to releasably anchor suture "S" also serve as a cannulated needle stopper to prevent cannulated needles 160, 162 from extending beyond free ends 140, 142 of arm members 132, 134, respectively.

Figure 8:
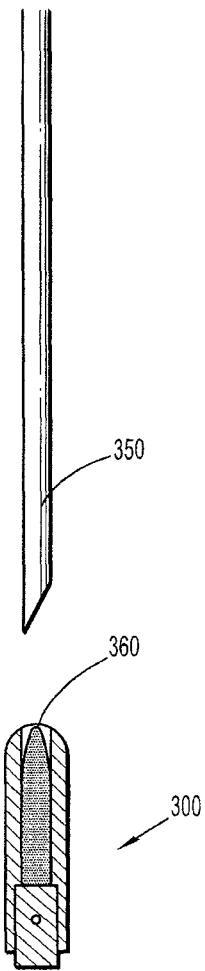
FIG. 8 is a side view of a ferrule assembly for use with the suturing device of FIG. 1.

With particular reference to FIG. 4, a pair of rods 164, 166 each having catching structure coupled to a distal end portion thereof is provided. Catching structure may be, for example, a hook 170. However, other catching structure may be employed. For example, a ferrule assembly 300, as shown in FIG. 8, may be disposed adjacent free ends 140, 142 of arm members 132, 134, respectively. Ferrule assembly 300 is configured to releasably retain a ferrule 360 which is adapted to retain a portion of suture "S." A distal end of a needle 350 is configured to engage ferrule 360 within ferrule assembly 300 for removal of ferrule 360 from ferrule assembly 300 along with suture "S". Ferrule 360 frictionally engages with open distal end of needle 350. However, it is further contemplated that needle 350 may also engage ferrule 360 through, for example, magnetic or adhesive, engagement.

Rods 164, 166 are dimensioned to slidably extend through lumens of cannulated needles 160, 162. Rods 164, 166 that extend through lumens of cannulated needles 160, 162 are directed towards attaching members 144, 146 on first surface 152 of introducer guard member 130. By utilizing hooks 170 provided at the distal end portions of rods 164, 166, a surgeon may manipulate rods 164, 166 from a relatively remote location to capture the looped ends of suture "S" anchored to attaching members 144, 146. Subsequently, rods 164, 166, now engaging looped ends of suture "S," may be pulled proximally and out of trajectory guide 120, thereby disengaging looped ends of suture "S" from attaching members 144, 146 as shown FIG. 5. Consequently, the looped ends of suture "S" are pulled out of trajectory guide 120. Thereafter, looped ends of suture "S" are disengaged from rods 164, 166 such that cannulated needles 160, 162 may be withdrawn from trajectory guide 120. Upon extraction of rods 164, 166 and cannulated needles 160, 162 from trajectory guide 120, suturing instrument 100 is now ready to be removed from the opening in tissue "T" by first releasing the lock mechanism on trajectory guide 120 and retracting arm members 132, 134 of introducer guard member 130 to the first position. Thereafter, suture "S" that is connected to mesh 148 is ready to be tied to appose tissue "T," as will be discussed in greater detail below.

Operation of suturing device 100 will now be described with reference to FIGS. 1-7. In the description that follows, it is assumed that suturing device 100 is in the ready-to-use condition. Specifically, mesh 148 has been secured to second surface 150 of arm members 132, 134 by suture "S" which is releasably anchored to attaching member 144, 146 of arm members 132, 134, respectively (as best seen in FIG. 4).

Initially, with introducer guard member 130 in a retracted position, substantially in alignment with longitudinal axis "A-A" of elongate shaft 110, suturing device 100 is inserted into an opening in tissue "T" created by, e.g., trocar, obturator, or the like. A distal portion of elongate shaft 110 is first inserted through the opening in tissue "T" and trajectory guide 120 is securely wedged into the opening in tissue "T." The surgeon adjusts the distance between trajectory guide 120 and introducer guard member 130 based on the anatomy of the patient by moving trajectory guide 120 along elongate shaft 110. Once the desired distance is achieved, the locking mechanism on trajectory guide 120 is utilized to securely anchor trajectory guide 120 to a desired position along elongate shaft 110. Alternatively, the surgeon may position trajectory guide 120 in the opening in tissue "T" and move elongate shaft 110 relative to trajectory guide 120 to adjust position of introducer guard member 130. Trajectory guide 120, as shown in FIG. 4B, may include additional set of bores 122a, 124a, each defining longitudinal axis "K-K," "L-L" in order to account for the change in angle when the distance between trajectory guide 120 and introducer guard member 130 is varied. It is contemplated that trajectory guide 120 may further include a plurality of bores to further accommodate a wide range of patients and procedures being performed. Moreover, elongate shaft 110 may include indicia related to distance between trajectory guide 120 and introducer guard member 130 indicating which bores to use. The tapered configuration of trajectory guide 120 facilitates secure anchoring thereof to the opening in tissue "T." Upon anchoring trajectory guide 120 to the opening in tissue "T," aim members 132, 134 of introducer guard member 130 that are hingedly coupled to distal end portion 112 of elongate shaft 110 are deployed in the direction of arrow "X" shown in FIG. 1 by an actuating mechanism. It is also contemplated that introducer guard member 130 coupled to elongate shaft 110 may also include other linkages such as cam paths, rotating elements, etc.

The actuating mechanism may include a pneumatic actuating mechanism or a hydraulic actuating mechanism. The pneumatic actuating mechanism may use pressurized gas, e.g., compressed air, carbon dioxide, or the like, to deploy arm members 132, 134 from the retracted position. On the other hand, the hydraulic actuating mechanism may use liquid, e.g., sterilized water, saline, or the like, to trigger the mechanical motion of deploying arm members 132, 134. The pneumatic and hydraulic actuating mechanisms may be portable or non-portable mechanisms.

Deployed arm members 132, 134 are now oriented in a manner substantially orthogonal to longitudinal axis "A-A," thereby defining transverse axis "B-B." At this point, longitudinal axes of bores "D-D," "E-E" align with attaching members 144, 146 disposed adjacent free ends 140, 142 of arm members 132, 134, respectively.

With reference to FIG. 3, cannulated needles 160, 162 each having lumens therethrough are slidably inserted through bores 122, 124, respectively. Bores 122, 124 that define longitudinal axes "D-D," "E-E," respectively, guide cannulated needles 160, 162 through tissue "T" and toward respective attaching members 144, 146. Cannulated needles 160, 162 are prevented from extending beyond free ends of arm member 140, 142 by the respective attaching members 144, 146. Upon reaching attaching member 144, 146, cannulated needles 160, 162 come in contact with first surface 152 of introducer guard member 130.

With reference to FIG. 4, upon placing cannulated needles 160, 162 having lumens therethrough on first surface 152 of arm members 132, 134, rods 164, 166 are slidably inserted through the lumens of cannulated needles 160, 162, respectively. Rods 164, 166 exit cannulated needles 160, 162, adjacent attaching member 144, 146 having looped ends of suture "S" anchored thereto. Catching structure such as hooks 170 provided at distal end portions of rods 164, 166 are utilized to capture the looped ends of suture "S" by manipulating rods 164, 166 from a relatively remote location. Looped ends of suture "S" releasably anchored to attaching members 144, 146 are captured by hooks 170 and disengage from attaching members 144, 146.

Figure 6:
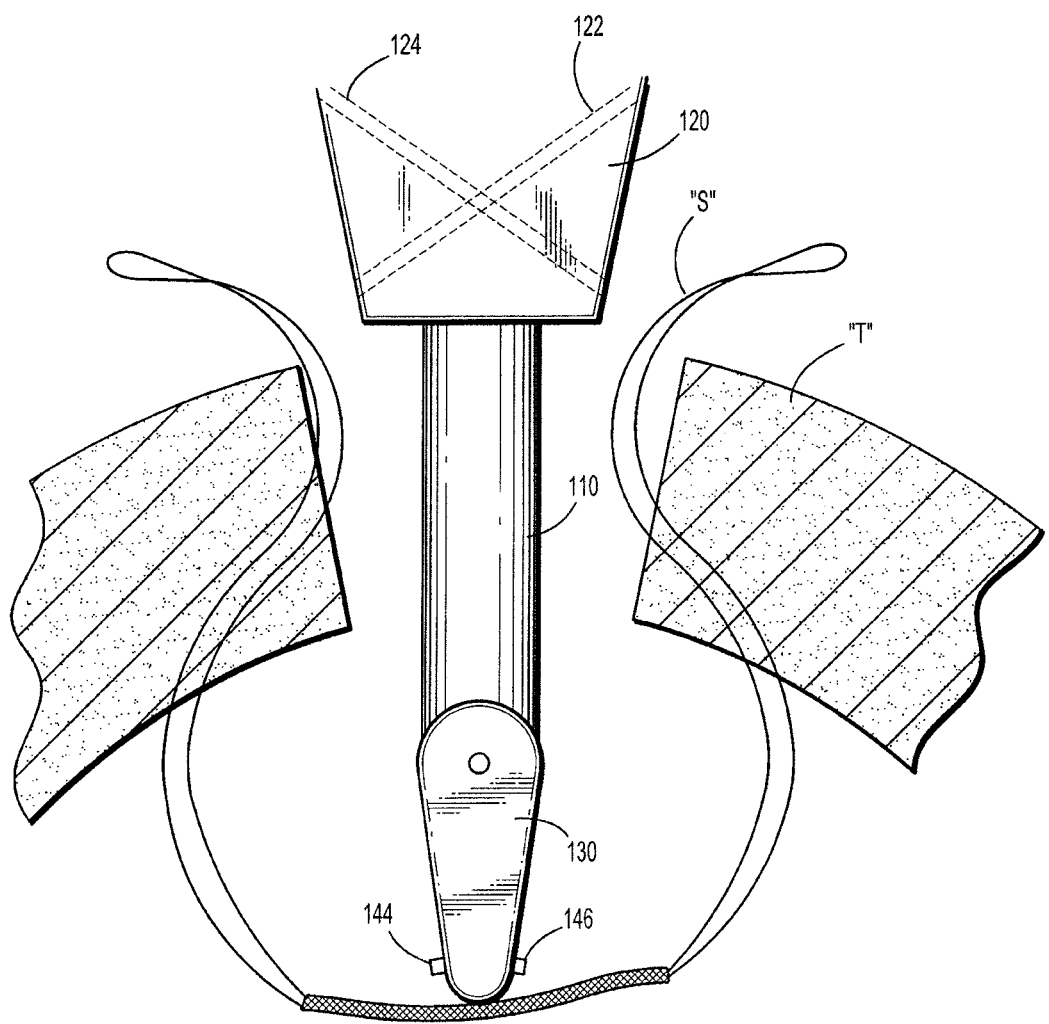
FIG. 6 is a side view of the suturing device of FIG. 5 illustrating extraction of the suturing device from an opening of tissue.
Figure 7:
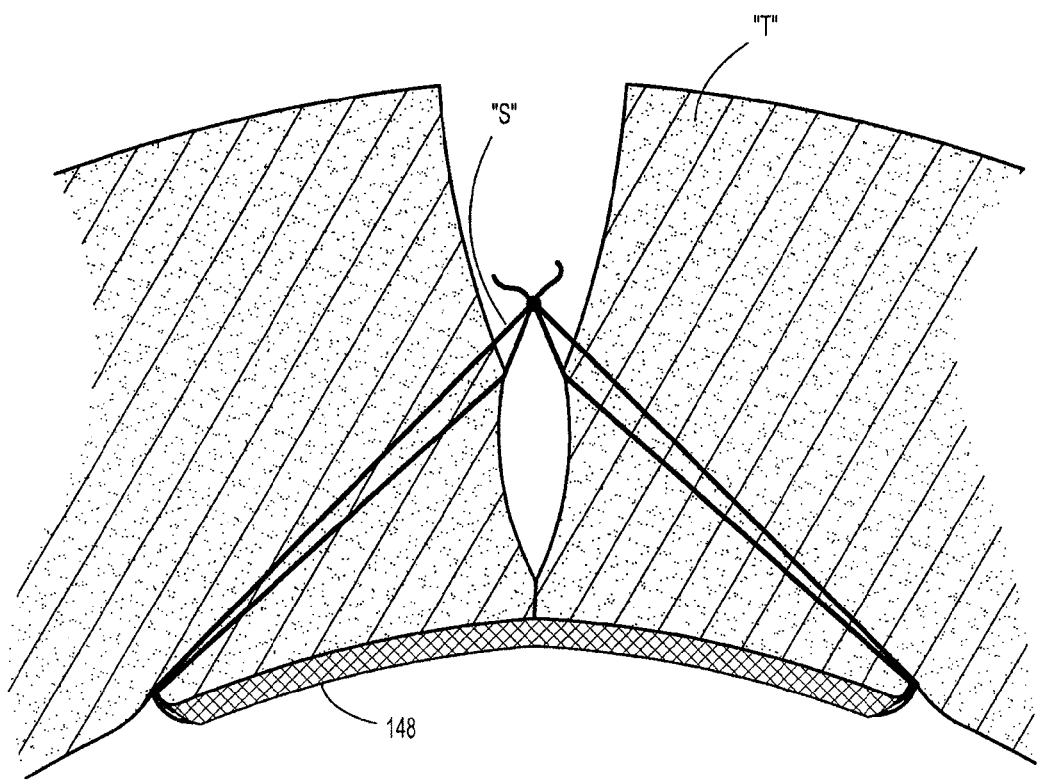
FIG. 7 is a cross-sectional view of tissue of FIG. 6 apposed by the suture.

With reference to FIG. 5, the looped ends of suture "S" now disengaged from attaching members 144, 146 are proximally pulled through lumens of cannulated needles 160, 162, respectively, until the ends of suture "S" have been withdrawn from bores 122, 124 adjacent proximal end portions of trajectory guide 120. Following the extraction of the looped ends of suture "S," cannulated needles 160, 162 and rods 164, 166 are removed from trajectory guide 120 such that suture "S" now directly pierces through tissue "T." Upon removal of cannulated needles 160, 162 suturing instrument 100 may be proximally pulled out of tissue "T" by first placing the arms 132, 134 in the retracted position and releasing the locking mechanism on trajectory guide 120 to permit trajectory guide 120 to be translatable along elongate shaft 110. Trajectory guide 120 now translatable along elongate shaft 110 is proximally translated to disengage from the opening in tissue "T." At the same time, elongate shaft 110 may be slightly pushed distally to provide sufficient space for arm members 132, 134 to retract to the initial position in which introducer guard member 130 is in substantial alignment with longitudinal axis "A-A." As shown in FIG. 6, trajectory guide 120 in substantial alignment with longitudinal axis "A-A" is pulled out of the opening in tissue "T" by which the looped ends of suture "S" exit bores 122, 124 from the distal end portions of trajectory guide 120. At this time, suturing instrument 100 is withdrawn from the opening in tissue "T," while leaving suture "S" containing mesh 148 and directly piercing tissue "T" in place.

After the removal of suturing instrument 100 from the opening of tissue "T," suture "S" having mesh 148 remains in place with respect to tissue "T" and is now ready to be tied to appose tissue "T," as will be discussed in greater detail below. As discussed above, the degree of angle of bores 122, 124 with respect to longitudinal axis "A-A" and the length of arm members 132, 134 may be tailored to meet the suitable needs of the procedure being performed. For example, a greater degree of angle needs to be selected if a bigger mesh 148 is to be chosen, in order to ensure that mesh 148 tightly covers against the posterior side of the opening of tissue "T." Moreover, by choosing a greater degree of angle, suture "S" enters the posterior side of tissue "T" away from the opening in tissue "T" which may inhibit tearing of sutured tissue "T." With reference to FIG. 7, the looped ends of suture "S" are now tied together to appose tissue "T," while providing mesh 148 to the second surface of tissue "T."

Figure 9:
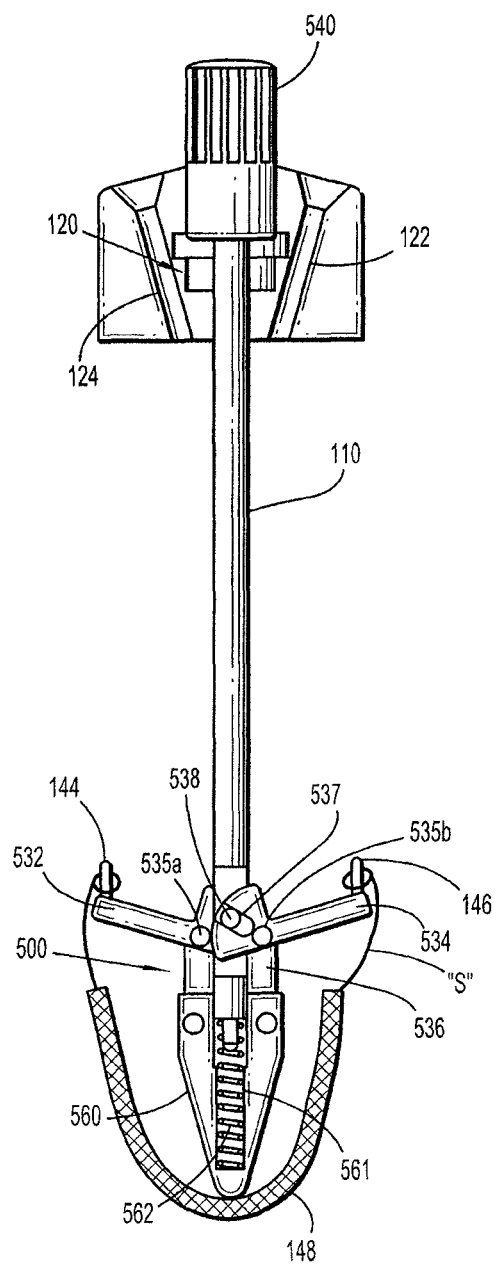
FIG. 9 is a side view of an actuation device for use with the suturing device of FIG. 1

It is contemplated that an actuator assembly 500 as shown in FIG. 9 may be used with suturing device 100 of the present disclosure to actuate arm members 132, 134 from the first position to the second position or vice versa. Actuator assembly 500 includes a knob 540 and a base assembly 560. Knob 540 and base assembly 560 are coupled by elongate shaft 110. Base 560 defines a bore 561 in which a biasing member 562 is housed in longitudinal alignment with shaft 110. Aim members 532, 534 are hingedly coupled to an engaging portion 536 of base 560 about pivots 535a, 535b, respectively. Each arm member 532, 534 defines a slot 537 for slidably accommodating therein pin 538 protruding transversely from shaft 110 (only slot 537 defined in arm member 534 is shown in FIG. 9). As knob 540 is pressed distally by the operator, pin 538 of shaft 110 translates distally with respect to engaging portion 536 of base 560, and slots 537 urge respective members 532, 534 to the retracted position (first position). At this time, arm members 532, 534 are longitudinally aligned with shaft 110 and are ready to be inserted into the opening in tissue "T." It is further contemplated that a locking mechanism (not shown) may be provided to lock arm members 532, 534 in the first position. Upon releasing of knob 540 by the operator, biasing member 562 moves shaft 110 proximally with respect to engaging portion 536 of base 560 such that pin 538 translates proximally, which in turn urges arm members 532, 534 to be deployed to the second position, as shown in FIG. 9. Mesh 148 can also be attached to arm members 532, 534 by suture "S." As discussed above, attaching members 144, 146 in a form of prongs or pins configured to releasably retain the ends of suture "S" may be provided on arm members 532, 534.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A suturing device comprising:
an elongate shaft defining a longitudinal axis;
a trajectory guide mounted on the elongate shaft, the trajectory guide defining first and second bores therethrough, the first and second bores each having a proximal end, at least one of the first and second bores extending obliquely with respect to the longitudinal axis; and
an introducer guard member operatively coupled to the elongate shaft, the introducer guard member including at least one arm member, the at least one arm member being movable between a first position in which the at least one arm member is substantially in alignment with the longitudinal axis and a second position in which the at least one arm member is off-set with respect to the longitudinal axis, wherein the trajectory guide is movable along the longitudinal axis and independently of the introducer guard member, and the proximal ends of the first and second bores diametrically oppose each other.

2. The suturing device of claim 1, wherein the at least one arm member is hingedly connected to the elongate shaft.

3. The suturing device of claim 1, wherein the at least one arm member is hingedly connected to a distal portion of the elongate shaft.

4. The suturing device of claim 1, wherein the trajectory guide includes a locking mechanism for securely anchoring the trajectory guide to a position along the elongate shaft.

5. The suturing device of claim 1, wherein the at least one arm member includes an attaching member configured for releasably retaining a suture.

6. The suturing device of claim 5, wherein the attaching member is on a first surface of the at least one arm member.

7. The suturing device of claim 6, wherein one of the first and second bores is aligned with the attaching member when the at least one arm member is in the second position.

8. The suturing device of claim 6, further comprising a mesh disposed on a second surface of the at least one arm member when the at least one arm member is in the second position.

9. The suturing device of claim 8, wherein the suture attaches the mesh against the second surface of the at least one arm member when the at least one arm member is in the second position.

10. The suturing device of claim 5, wherein the attaching member is disposed adjacent a distal end of the at least one arm member.

11. The suturing device of claim 10, wherein the at least one of the first and second bores is aligned with the attaching member when the at least one arm member is in the second position.

12. The suturing device of claim 5, further comprising a cannulated needle defining a lumen therethrough, wherein one of the first and second bores of the trajectory guide is dimensioned for receiving the cannulated needle therethrough.

13. The suturing device of claim 12, further comprising a rod, the lumen of the cannulated needle being configured for receiving the rod therethrough.

14. The suturing device of claim 13, wherein the rod includes a catching structure for capturing the suture releasably retained by the attaching member.

15. The suturing device of claim 14, wherein the catching structure is disposed at a distal portion of the rod.

16. The suturing device of claim 15, wherein the catching structure is a hook.

17. The suturing device of claim 1, wherein the introducer guard member in the second position is substantially orthogonal with respect to the longitudinal axis.

18. The suturing device of claim 1, wherein the trajectory guide is longitudinally tapered with respect to a width thereof.

19. The suturing device of claim 1, wherein the introducer guard member is longitudinally tapered with respect to a width thereof.

20. The suturing device of claim 1, wherein the at least one arm member is longitudinally tapered with respect to a width thereof.

21. The suturing device of claim 1, wherein the trajectory guide surrounds a portion of the elongate shaft.

22. The suturing device of claim 1, wherein one of the first and second bores extends between proximal and distal portions of the trajectory guide.

* * * * *